United States Patent [19]

Karler et al.

[11] 4,169,139
[45] Sep. 25, 1979

[54] GLYCO/PROTEINACEOUS MATERIALS DERIVABLE FROM BEEF LIVER AND OTHER TISSUES USEFUL FOR THE TREATMENT OF TOXIC AND ALLERGIC CONDITIONS

[76] Inventors: Arthur Karler, 933 Shevlin Dr., El Cerrito, Calif. 94530; Milton P. Ream, deceased, late of Oakland, Calif.; by Allen K. Ream, executor, 288 Miramontes Rd., Woodside, Calif. 94062

[21] Appl. No.: 703,072

[22] Filed: Jul. 6, 1976

Related U.S. Application Data

[63] Continuation-in-part of Ser. No. 512,714, Oct. 7, 1974, abandoned.

[51] Int. Cl.² .............................................. A61K 35/40
[52] U.S. Cl. .................................................... 424/106
[58] Field of Search ...................... 424/106; 260/112 R

[56] References Cited

U.S. PATENT DOCUMENTS

| 3,624,251 | 11/1971 | Huber | 260/112 R |
| 3,701,768 | 10/1972 | Fortini et al. | 260/112 R |
| 3,758,682 | 9/1973 | Huber et al. | 260/112 R |

FOREIGN PATENT DOCUMENTS 1205906  9/1970  United Kingdom .................... 424/106

OTHER PUBLICATIONS

Timar et al., Biochemical Pharmacology, vol. 18, No. 7, (Jul. 1969), pp. 2278-2279.

*Primary Examiner*—Darrell B. Moyer
*Attorney, Agent, or Firm*—Edward B. Gregg

[57] ABSTRACT

Mucoprotides (i.e., complex compounds of protein with carbohydrates and carbohydrate derivatives) derived from animal tissues, for example, mammalian liver by a succession of extractive steps including treatment with acetone to produce three layers or phases of which the upper two are separated and further processed, the bottom layer being discarded. The retained layers are further treated to purify and de-antigenize them. The product is useful for treatment of allergic conditions, as a detoxicant and for treatment of narcotics addiction.

6 Claims, 4 Drawing Figures

GLYCO/PROTEINACEOUS MATERIALS DERIVABLE FROM BEEF LIVER AND OTHER TISSUES USEFUL FOR THE TREATMENT OF TOXIC AND ALLERGIC CONDITIONS

This application is a continuation-in-part of our co-pending application, Ser. No. 512,714 filed Oct. 7, 1974, now abandoned, entitled "GLYCO/PROTEINACEOUS MATERIALS DERIVABLE FROM BEEF LIVER AND OTHER TISSUES USEFUL FOR THE TREATMENT OF TOXIC AND ALLERGIC CONDITIONS."

This invention relates to certain derivatives of animal tissues, notably mammalian liver, but also certain other organs, such derivatives having biological activity including de-toxifying effects, utility in the treatment of allergic conditions, and the treatment of narcotics addiction.

The invention relates also to similar naturally occurring materials derived from other sources such as yeast. Such materials are identifiable by their infrared transmittance spectrum.

This invention relates more particularly to proteinaceous derivatives of mammalian liver (and of other sources) which has a protide component as the principal component but which also has a significant carbohydrate component hereinafter referred to as mucoid, the biological and therapeutic properties of these derivatives being dependent on the chemical combinations of protide and mucoid.

By the term "protide" is meant not only protein but amino acids and oligopolypeptides. By "mucoid" is meant certain low molecular weight carbohydrates and derivatives such as hexoses (for example, glucose, galactose, mannose), sialic acids, hexoseamines such as glucoseamine and galactoseimine, fucose, etc.

Several groups of workers have, since the 1940's, treated mammalian liver by generally similar procedures starting with macerated liver parenchyma—i.e., liver tissue freed of fibrous material, fat and blood vessels. In this procedure, by the systematic application of aqueous solutions of inorganic salts as selective precipitants of unwanted (discarded) components, treatment in step-wise manner with acetone and further processing of one or more (but less than all) of the phases resulting from acetone treatment and suitable purification of the selected phase or phases (as, for example, by dialysis) there have been isolated biologically active components of the liver.

For example, Mohamed and Greenberg publishing in 1945 in Archives of Biochemistry, vol. 8, p. 349 set forth a procedure which is the genesis of all later procedures and which results in the isolation of the enzyme arginase.

Fortini, Blair and Grodsky in U.S. Pat. No. 3,701,768 have described a procedure much like that of Mohamed and Greenberg up to a point but with certain differences. For example, the acetone step is carried out to produce three phases of which only the upper layer or phase is separated and processed and the middle and bottom layers or phases are discarded. The separated upper phase is treated to precipitate a protein component, is then subjected to dialysis, then to a heating step to destroy antigens and then to fractionating of the protein component, as by chromatography, to produce a highly purified protein fraction.

Other workers in this field include Huber (production of Orgotein, see U.S. Pat. No. 3,624,251) and Wesley Irons (see British patent application No. 5242/57).

Difficulties encountered in products of such character which have been intended for therapeutic purposes (Fortini et al, Huber, and Irons) have included lack of uniformity in that different lots have had greatly different biological activity and further lack of stability.

It is an object of the present invention to provide improved methods of deriving a biologically active, medically useful (for treatment of animals and human beings) material which is more consistent in its significant biological activity and which is more stable than some, if not most or all, of the earlier preparations referred to above.

It is another object of the invention to provide a method of producing biologically active mucoprotide material from mammalian liver and the like which results in higher yields than methods used heretofore as well as minimization of bacterial contamination resulting in pyrogenicity which gives a non-usable clinical product.

The above and other objects of the invention will be apparent from the ensuing description and the appended claims.

We have found that much more consistently active products at higher yields and having enhanced stability result from a procedure described below.

PREPARATION

A. Starting Materials

Mammalian liver, placenta, spleen, kidney, pancreas, and pituitary glands are some of the preferred sources of these biologically-active mucoprotides. Liver and placenta are preferred. However, tests indicate their presence in significant amounts in all types of mammalian tissue. The source material should come from healthy animals and should be treated mechanically to remove extraneous fat, fibrous material, and the like, leaving primarily the tissue characteristic of the organ, for example, parenchyma in the case of liver.

I. Autolysis

Defibrinated, decapsulated, defatted yound steer liver is obtained from healthy animals under clean conditions as described above. The procedure described herein is based upon 3 kilograms of prepared liver (parenchyma). This liver parenchyma is diced and macerated or homogenized in a Waring blender with 600 cc. of solution containing 50 grams of sodium acetate per liter and 15.4 grams of manganous sulphate per liter. This homogenate is stirred vigorously at room temperature (20° to 22° C. ) for 24 hours. This homogenate-autolysate is strained through one layer of gauge #80 strainer.

II. Bulk Removal of Extraneous Protein and Protein Associated Material

This strained liquid autolysate is treated with 3000 cc. of 4.575% lead acetate; stirred vigorously for 35 to 40 minutes and let stand for at least 1 hour at room temperature. The liquid is then centrifuged and the supernatant fluid is adjusted to pH 8.3–8.4 with 2.5 liters of 0.2 N NaOH (or whatever amount may be required for this pH adjustment). Let liquid stand for at least 2 hours at room temperature; then clarify liquid by filtration and/or centrifugation. Add to supernatant fluid one-third volume of saturated ammonium sulphate (780 grams/liter); let stand for 3 to 4 hours at room temperature. Then carefully filter and centrifuge; test for absence of lead. Save clear supernate.

III. Acetone Treatment and Dialysis of the Selected Phase

Acetone to 35% by volume is added to the lead-free supernate from Step II. The liquid is allowed to stand 4 to 6 hours at room temperature. It is then filtered and centrifuged. More acetone is then added to the supernate to give 60% acetone by volume. Let stand for 6 hours at room temperature. Three layers will be formed; the bulk of the arginase or arginase-associated protein will be in the middle layer. Siphon off the two top layers; discard lowest layer. To the two top layers add an equal volume of acetone. A gummy precipitate will form; let stand 4 to 6 hours at room temperature. Isolate the precipitate. The precipitate is dissolved with 0.1 M $K_2HPO_4$ adjusted to pH 8.5; use 750 to 1000 cc. of adjusted buffer for dissolution. Place this solution in dialyzing bags and dialyze against pure water with frequent water changes and continuous agitation to speed up dialysis until material in the dialysis bags tests free of minerals (e.g., a conductivity test of not more than 1 ppm). The time required for dialysis will depend upon the physical parameters of the dialysis system but should be accomplished within 48 hours to minimize the possibility of significant losses due to a slow disintegration of the product at this stage of isolation of the product of this invention. Remove solution from the dialysis bags and centrifuge; save the supernate.

The two top layers separated from the bottom layer before the second acetone addition, instead of being further treated as described above, may be used without further purification as an edible liver extract for buccal use by lyophilizing them and packaging the resulting dry powder in buccal form as wafers or thin tablets made with an appropriate inert excipient. The amount of lyophilized product would be determined by bioassay of the active product ingredient present in these two top layers. A buccal dosage of ten times the parenteral form is presently recommended. Suitable excipients are lactose, starch and cellulose, and suitable proportions of lyophilized material are 5 to 25% based on total buccal product.

IV. De-antigenization and Stabilization

Returning now to the protocol for the parenteral material, place this supernate in a water bath maintained at 47°–49° until all extraneous, unstable and antigenic materials are precipitated (large flakes); this is usually accomplished in 3 to 5 hours. Centrifuge at high speed until there is a clear supernate. An aliquot of the supernate is removed for determination of concentration of active component and for standardization. With some preparations depending on the tissue and species of origin, this step of de-antigenization can be eliminated; this is especially true of bovine and human placental preparations. As a matter of routine practice, however, it is best to go through this de-antigenization procedure unless a small aliquot of the production batch is first put through this step as a safety test to be certain that no antigenic proteinaceous material is present.

The clear supernate resulting from centrifugation is sterile-filtered in a sterilizing membrane filtration system and stored in a freezer or lyophilized under sterile conditions. The yield of concentrate will vary but is usually in the range of 2 liters of a 1 to 2% solution, or 20 to 40 grams. A typical preparation will have a human parenteral dosage range from 0.5 mg to 1.5 mg. per 75 kg. adult, depending on the biological activity of a particular batch. The usual parenteral (I.V.) dosage form is a 5 cc. ampoule.

V. Final Purification

The final purification of the product is effected by a novel step just prior to ampoulization for clinical usage. The concentrate is appropriately diluted to final concentration with pyrogen-free, sterile water and left to stand at room temperature (65° to 75° F.) for at least 8 days or until no further pinkish precipitate forms. This bulk solution is sterile-filtered to remove the precipitate, reassayed and standardized, and put into final form for clinical usage.

ANALYSIS

Because of the complicated, diverse structural relationships of the group of substances known as mucoprotides, several different approaches had to be used to "tease" these complex molecules apart in order to minimize and/or account for the losses during their hydrolysis or breakdown to their simple compositional subunits. The very elaborateness and the necessity for gentle "pretreatment" of the mucoprotides to minimize loss of subunits emphasize the differences of the product of this invention from the simple "pure" protein of the Fortini-Grodsky-Blair patent and the simple metalloprotein of the Huber-Schulte patents. Specifically, a much more gentle and discriminating hydrolytic technique had to be used for the mucoid or carbohydrate moiety as compared with the conventional vigorous hydrolysis of a pure or simple protein. The general procedure for the qualitative and semi-quantitative pretreatment and analysis of the mucoid or carbohydrate moiety of these mucoprotides is similar to the basic procedure described by Richard J. Winzler in the Ciba Foundation symposium "The Chemistry and Biology of Mucopolysaccharides," pp. 258–261, Little Brown & Co., Boston, 1958; for quantitative results, more rigorous analytical methods for the mucoid subunits are used as indicated in the following descriptions.

The analytical procedure employed for the mucoid moiety of the mucoprotides is as follows: A 20 milligrams sample of mucoprotide in its final form (i.e., the active component resulting from Step V of the preferred preparative protocol) is mixed with 20 milliliters of 1.0 molar hydrochloric acid and the mixture heated for 15 minutes at 100 degrees Centigrade. This procedure results in the release of maximum amounts of sialic acid(s) and fucose with only about 5% hydrolysis of the protide moiety. Simultaneously, another 20 milligram sample of mucoprotide is treated the same as the first sample but the hydrolysis is continued for 1 hour, thus resulting in the maximum release of hexoses and hexoseamines with only about 15 to 20% hydrolysis of the protide moiety. Aliquots of these treated samples are immediately subjected to dialysis (or ultrafiltration) and the dialysates (or ultrafiltrates) evaporated to dryness, and chromatographed, using a descending solvent system of ethyl acetate:pyridine:water in the ratio of 10:4:3 parts by volume and the resulting chromatogram air-dried and stained with a solution of aniline exalate. The spots are identified by checking positions with corresponding known standards and quantitated by analysis of the chromatogram by a quantitative analytical comparator and/or by quantitative analysis of the eluate of the individual compounds. The specific analytical methods are further detailed in the following references: R. J. Winzler, "Determination of Serum Glycoproteins," *Methods of Biochemical Analysis*, vol. II, pp. 279-311, Interscience Publishers, N.Y., 1955; Leonard Warren, "The Thiobarbituric Acid Assay of Sialic Acids," *Journal of Biological Chemistry*, vol. 234, pp. 1971-1975 (1959); C. J. M. Rondle and W. T. J. Morgan, "The Determination of Glucosamine and Galactose-amine," *Biochemical Journal*, vol. 61, pp. 586-589 (1955).

The analytical procedure employed for protide moiety of the mucoprotides is as follows: Because of the presenece of carbohydrate or mucoid, excessively harsh or prolonged methods of hydrolysis must be avoided to minimize losses of constitutent amino acids as a result of the so-called "browning reaction" involving the condensation of released mucoid and protide subunits to give dark by-products. Mucoprotides of lower carbohydrate content (0.1% to 10%) such as those obtained from some mammalian livers can usually be hydrolyzed directly by the procedure described below. Mucoprotides of higher carbohydrate content (10% to 40%) such as those obtained from some mammalian placentas should be subjected to a preliminary mild hydrolysis such as that employed above for the release of carbohydrate subunits (i.e., 1 hour at 100 degrees Centigrade in 1 molar hydrochloric acid), and then subjected to dialysis or ultrafiltration to remove the bulk of the released carbohydrate or mucoid materials; such a preliminary hydrolysis step will remove the bulk of the interfering carbohydrate, thus minimizing losses of amino acids due to reaction with the excessive carbohydrates. The hydrolysis of the protide moiety to the constituent free amino acids is then effected by treating 20 milligrams of protide or protide equivalent (calculated by subtracting the percentage equivalent of carbohydrate if the carbohydrate content is greater than 10% of the intact mucoprotide) with 20 milliliters of triply distilled 6 molar hydrochloric acid in sealed Pyrex glass tubes at 105 degrees Centigrade for 20 hours. Tryptophan which is destroyed during acid hydrolysis is determined by alkaline hydrolysis using 20 milligrams of protide equivalent in 20 milliliters of 4 normal barium hydroxide at 110 degrees Centigrade for 60 hours. Once hydrolysis is completed, the amino acid mixtures are subjected to conventional ion-exchange analysis (G. R. Tristram and R. H. Smith, *Advances in Protein Chemistry*, vol. 18, pp. 227-235, Academic Press, N.Y., 1963).

Typical Analyses are as follows: Amino Acid Analysis:

|  | Beef Liver Mucoprotide percent by weight | Human Placenta Mucoprotide percent by weight |
|---|---|---|
| Alanine | 5.3 | 2.8 |
| Arginine | 5.7 | 7.0 |
| Aspartic acid | 7.4 | 6.0 |
| Cystine | 0.6 | 6.2 |
| Glutamic acid | 5.4 | 7.1 |
| Glycine | 6.5 | 2.4 |
| Histidine | 3.2 | 1.6 |
| Isoleucine | 4.0 | 2.0 |
| Leucine | 9.7 | 5.0 |
| Lysine | 8.6 | 3.9 |
| Methionine | 1.8 | 1.6 |
| Phenylalanine | 3.4 | 2.5 |
| Proline | 8.8 | 8.6 |
| Serine | 5.5 | 6.0 |
| Threonine | 5.0 | 5.3 |
| Tryptophan | 2.0 | 0.7 |
| Tyrosine | 1.2 | 2.9 |
| Valine | 7.2 | 5.5 |
| Amide-$NH_2$ | not determined | — |
| $NH_3$ | 2.9 | — |

Mucoid Analysis

This is rather variable, both as to total mucoid content and as to the proportions of the various mucoid entities. The total mucoid content (based on total dry weight of solids) may be as low as 0.1% or as high as 40%. Conditions affecting the total mucoid content are species of animal used as sources of tissue, type of organ or tissue employed, and the method of preparation. For example, active mucoprotide preparations obtained from mammalian placenta may give a much higher mucoid content than the corresponding mucoprotide obtained from liver or spleen or blood; also the mucoprotides obtained by the improved method of this invention will give mucoprotides with significantly higher mucoid content than that obtained by previous methods. Type of species of animal as well as the health of the animal will limit the final yields: e.g., human placenta seems to give consistently higher percentages of mucoid than that obtained from bovine placenta.

Typical mucoid components in typical proportions are as follows:

| Sialic Acid(s) | | 25% to 30% |
|---|---|---|
| Hexoseamines (probably acetylated) | | 25% to 30% |
| Glucoseamine | 15% | |
| Galactoseamine | 10% | |
| Hexoses | | 30% to 25% |
| Glucose | 10% | |
| Galactose | 12% | |
| Mannose | 8% | |
| Fucose | | 1% to 5% |

Figure 1:
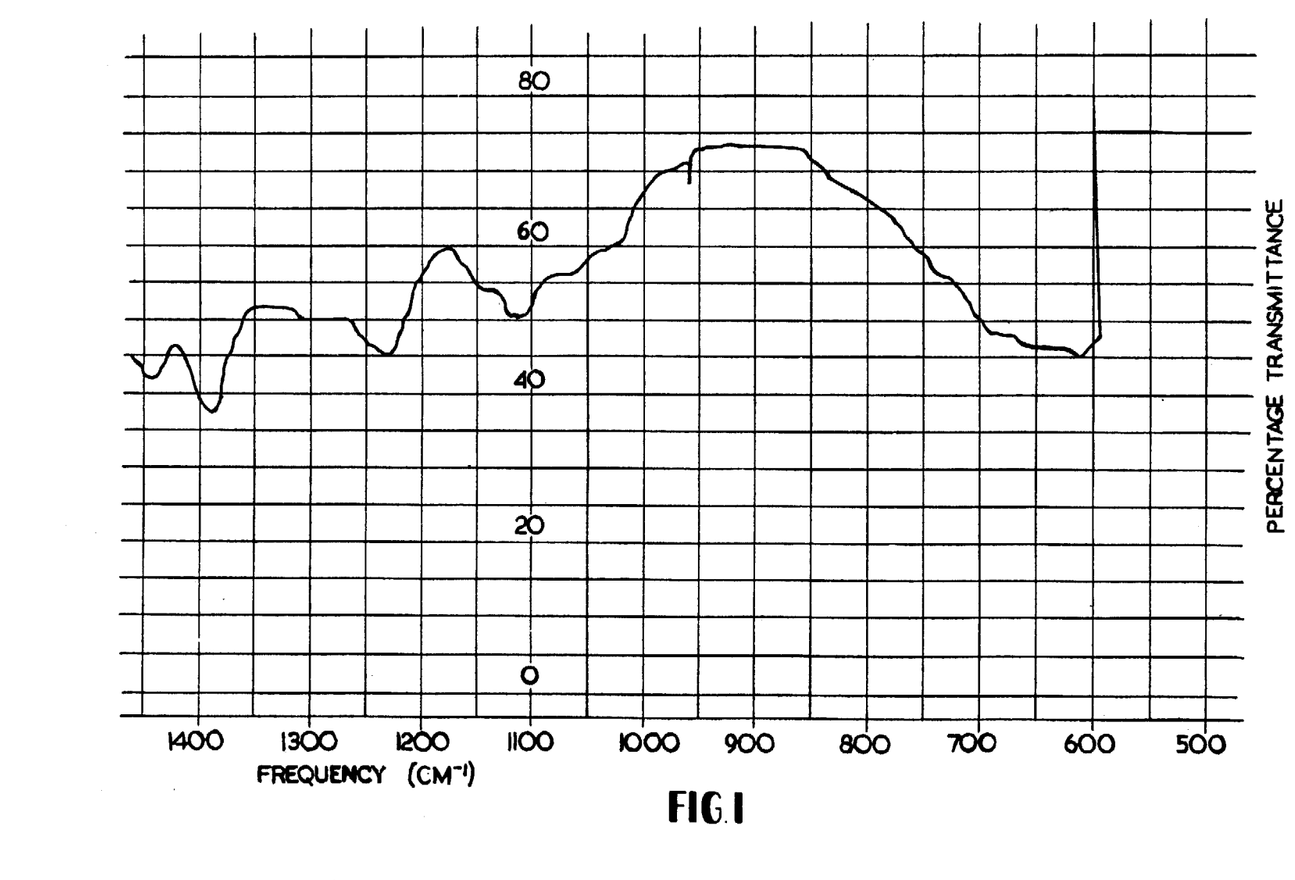
Figure 2:
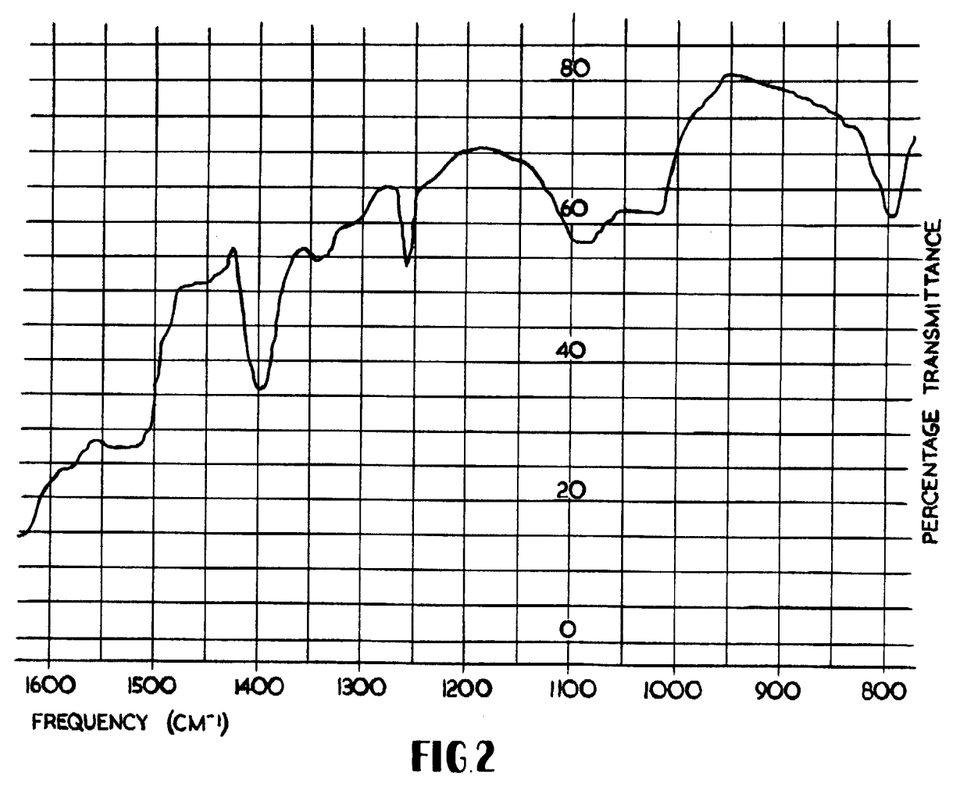
Figure 3:
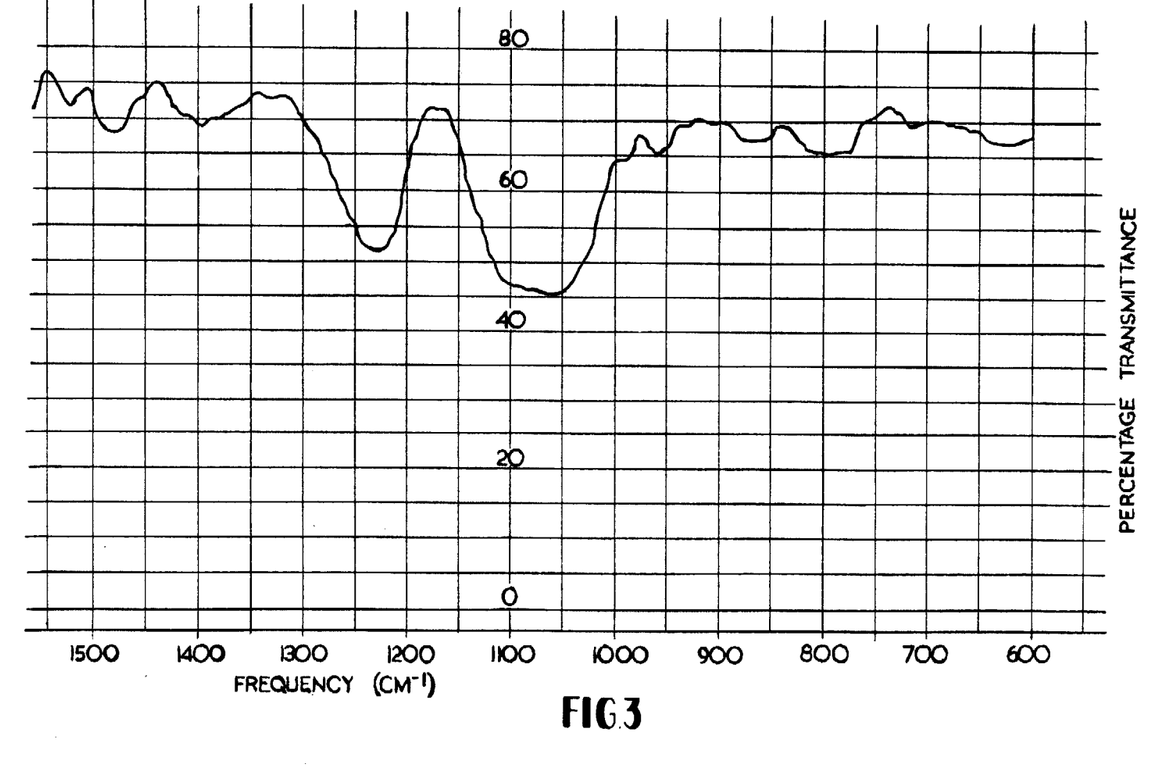
Figure 4:
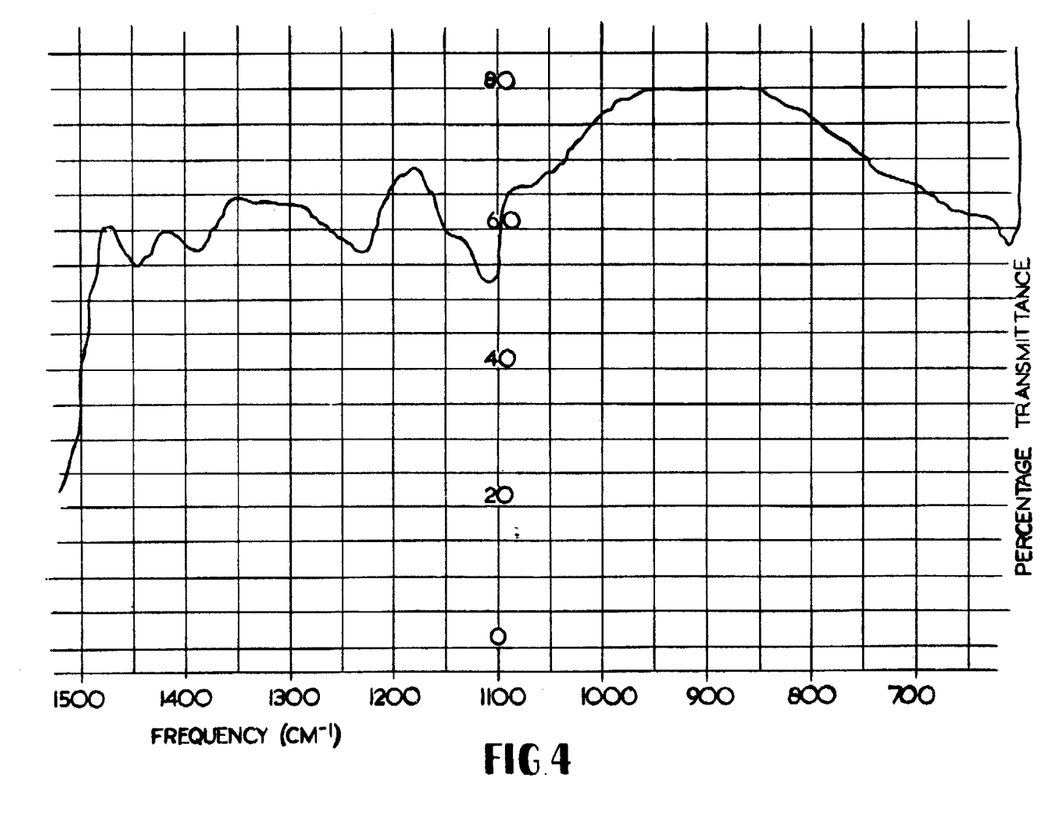

The material of the present invention is also characterized by its infrared transmittance spectrum. FIGS. 1, 2, 3 and 4 are segments of curves showing infrared transmittance of material prepared as described above. Ordinates are percentage transmittance and abscissae are in wave numbers. These spectral charts are, respectively, for material prepared for beef liver (FIG. 1), cow placenta (FIG. 2), yeast extract (FIG. 3) and commercially available trypsin (FIG. 4). The liver and placental material were prepared as described for beef liver above. Trypsin was the commercial crystalline material prepared as described in Hawk's Physiological Chemistry, 14th edition, page 441 (McGraw Hill publisher). Yeast extract was the ribonucleic acid preparation as described in Hawk, op.cit., pages 208 and 209. Surprisingly the yeast and RNA products contained mucoprotide material of the present invention. These products are taken up in a solution of the character used for clinical purposes and are subjected in solution to deantigenization and stabilization step IV above and preferably also to final purification step V.

As will be seen, each of these materials has a pronounced dip in its infrared spectrum at a frequency close to 1100 and in all cases between 1000 and 1200.

The remainder of the spectrum to the right and to the left of the 1000–1200 segment, including the spectrum beyond the range shown in the several figures, is typical of extracts prepared by the workers (Mohamed and Greenberg; Fortini, Blair and Grodsky; and Irons) mentioned above. It is the unique property of the material of the present invention that it has the characteristic transmittance spectrum at 1000–1200 as shown in the figures.

The infrared spectrophotometric analyses of the mucoprotide preparations were performed on the standard commercially available Perkin-Elmer 401 recording spectrophotometer by compressing the thoroughly mixed mucoprotide powder and potassium bromide into a standard KBr pellet, the final concentration of mucoprotide being 1%. The infrared spectrophotometer was standardized for each curve against polystyrene.

Modes of Administration and Dosages

The product of the invention may be administered by all parenteral routes (intravenous, intramuscular, subcutaneous, intraperitoneal) and by oral administration including buccal. The solution described in Step V may be the form in which it is administered or the solution may be lyophilized and the dry product may be administered in dry form with an excipient such as lactose, starch and cellulose.

The consumer product for buccal use may be in the form of pills, tablets or wafers. An especially advantageous mode of administration is the buccal route wherein a pill, tablet, wafer or aqueous solution containing 10 mg to 15 mg by weight of the active material from Step III is held in the mouth between the gums and the cheeks. This route avoids or greatly diminishes digestive attack on the active materials; it avoids or lessens possible allergic reactions to parenteral administration; it enables the patient to treat himself; and it places these mucoprotides in the category of a nutritional supplement (e.g., liver or pancreatic extract) rather than a pure drug or pharmaceutical.

Recommended dosages are, as stated above, about 0.5 mg to 2.0 mg of active material per 50 kilograms of weight. Frequency of treatment depends upon such factors as type of illness, duration (acute or chronic) of illness, conjunctive therapy with other agents, age and nutritional status of patient.

Medical and Veterinary Utility

The material of this invention is useful for treatment and/or prevention of allergic and hypersensitive conditions, of toxic conditions, of untoward side effects of common drugs and for the treatment of drug addiction and alcoholism. The material is especially useful when the condition treated is associated with or results from impairment of liver function as when there has been a deterioration of the liver parenchyma. Examples of conditions that have been or may be successfully treated are effects of addictive drugs such as narcotic analgesics (e.g., heroin and cocaine); alcoholism; and untoward side effects of therapeutic drugs such as penicillin and chloromycetin.

Although various specific posologies have been established for such categories of clinical application, the most favorable prognosis is obtained where the use of mucoprotides is simultaneously supported by a nutritional regimen designed to maximize the rapid restoration of normal liver function by rebuilding the parenchyma of the liver. Accordingly, in more advanced or severely debilitated cases the best clinical responses are obtained by employing an appropriate mucoprotide posology plus a well-balanced diet including intensive supplementation with vitamins, bioflavinoids, and pre-digested protein (i.e., a balanced mixture of free amino acids) to insure rapid repair of damaged liver tissue; such a rapid response and recovery are especially important in alcoholic and narcotic addiction where sudden withdrawal of the drug can result in overwhelming patient-management problems and a high rate of recidivism.

As a specific example, a patient addicted to heroin and who suffered such excruciating withdrawal symptoms that he refused to withdraw from heroin again, was treated by I.V. injection of 1 cc injections twice daily, then at more widely spread invervals, and was put on an adequate diet strongly fortified with vitamins, bioflavinoids and amino acids. Bromosulfothalein was administered at the start of therapy and again after four weeks of therapy. (A normal liver clears bromosulfothalein (BSP) quickly whereas a damaged liver allows longer retention of BSP.) BSP retention of this patient was 28% at 45 minutes at the commencement of treatment and was reduced to 1.9% at 45 minutes after four weeks of treatment. Further, after four weeks this patient had no desire for hard durgs such as heroin.

Significance of Mucoid Components, etc.

We have found that highly purified protein derivatives of mammalian liver, for example, the 97% pure material suggested in Fortini U.S. Pat. No. 3,701,768, is less active and less stable than the mucoprotides of the present invention. Our product is a mixture of mucoprotidic proteinaceous materials and not a single or simple protein such as Orgotein (see, for example, U.S. Pat. No. 3,624,251) or Acutalyn (See Fortini U.S. Pat. No. 3,701,768). Further, our product has a significant mucoid component which is chemially bound in some manner or other to the protidic component. In some manner that is not presently understood, this mucoid component is essential for biological and therapeutic efficacy, contributes to stability and results in greater reproducibility of results from one lot to another.

Other Considerations

It will be noted that the upper two phases in Step III are employed in the present invention whereas the middle phase is discarded in accordance with Fortini U.S. Pat. No. 3,701,768. Further, in prior procedures, for example, that of Fortini, low temperatures and resultant long periods of processing are required, for example, temperatures of 5° C. and processing steps that require many weeks. In the process of the present invention, room temperatures are employed in most of the steps, the time required for processing is greatly diminished and yields are greater; also, the speed of the improved process is so much greater than the older processes that the chances of bacterial contamination (pyrogenicity) is greatly reduced.

A cruder form of the product of the present invention is that obtained during Step III and may be used with certain advantages as a buccal product rather than an injectable or parenteral product. The buccal product consists of the top two layers in Step III; this semi-purified material usually contains significant amounts of extraneous proteinaceous contaminants which will usually induce severe anaphylactic responses if used parenterally; hence this crude form is not a practical injectable product. This crude form of the product may, however, be effective buccally where these anaphylactoid proteinaceous substances (contaminants) will not be absorbed as such by the buccal membranes in the mouth but will eventually be digested by the enzymes of the gastrointestinal tract, whereas therapeutically significant amounts of mucoprotide will be absorbed by the buccal membranes into the body.

BIOASSAY

Heretofore persons working the field of derivation of medically useful proteinaceous materials from liver parenchyma and other tissues have striven to achieve a pure protein supposed to be the effective component of cruder products. In accordance with the present invention, a derivative of such tissue is produced (e.g., by a protocol such as described above), which consistently exhibits a significant and measureble in vivo function, that function being in liver damage due to one or more clearly defined causes and which is susceptible to reliable measurement. The causes are acute allyl alcohol intoxication and carbon tetrachloride poisoning of the liver; the subjects are laboratory rats of an accepted strain for laboratory investigation; and the test for effect on liver function is bromosulfothalein (BSP) clearance or observed liver damage of sacrificed animals.

BSP clearance is an accepted criterion of liver function. See, for example, Varley, *Practical Clinical Biochemistry*, pp. 293-294, Interscience Publishers, New York, 1958. BSP administered intravenously is readily detected in the blood stream after administration; it is cleared by the liver; a normal liver will clear the BSP quickly; damaged liver will clear BSP more slowly; and the time required to reduce BSP to a predetermined level is a reasonably quantitative measure of damage to liver function. Examination of the liver of sacrificed animals to which the toxic agent has been administered provides a semi-quantitative check. Details from tests will now be described.

(1) Liver Damage due to Allyl Alcohol Intoxication

Wistar male rats, weight range 180 to 200 grams in groups of 20 are treated with allyl alcohol administered by mouth in amounts of 0.4 ml of a 1% aqueous solution of allyl alcohol per 100 grams of animal weight. A group of animals are treated preventively with a mucoprotide solution of the present invention given subcutaneously at the doses of 1 ml per 100 grams of animal weight at 48, 24 and 1 hour before administration of allyl alcohol. Another group are treated curatively with the same doses of mucoprotide solution but given 1, 6, 24 and 30 hours after allyl alcohol administration. All groups are sacrificed 48 hours after allyl alcohol administration. A final mucoprotide injection is given 30 hours after intoxication because liver necrosis becomes clearly visible after 36 hours.

The results of three successive illustrative experiments are summarized in the table below.

| | (Acute Alyl Alcohol Intoxication), Grams of Damaged Liver Tissue | | |
|---|---|---|---|
| Experiment No. | Control | Preventive | Curative |
| I | 7.10 | 0.59 | 1.30 |
| II | 8.00 | 0.62 | 1.65 |
| III | 8.34 | 0.72 | 1.33 |
| | 70-80% | <10% | <20% |

Examination of the post mortem livers clearly revealed extensive perilobular liver necrosis. Mucoprotide treatment greatly diminished or eliminated the necrosis, whether used preventively or curatively. This hepato-protective action of the mucoprotide is clearly shown in the table above.

(2) BSP Clearance after Carbon Tetrachloride Administration

Carbon tetrachloride is administered subcutaneously twice weekly for three weeks in doses of 0.1 ml per 100 grams of animal weight to male Wistar rats of 150 to 200 gram weight divided into groups of 20 animals. The mucoprotide of the invention is administered subcutaneously in a dose of 0.5 ml per 100 grams of animal weight daily for five days after the end of the carbon tetrachloride administration. Twenty-four hours after the end of the mucoprotide treatment BSP is administered to both groups of animals (the treated and the untreated or control groups) intravenously using a solution of 1% BSP at a level of 0.5 mg of BSP per 100 grams of animal weight. Blood samples are removed after 1 and 10 minutes. The quantity of BSP in the serum is determined by modifying the clinical method described in Varley and the retention values are calculated with the formula:

$$\text{BSP retention} = \frac{\text{concentration of BSP at 10 minutes}}{\text{concentration of BSP at 1 minute}} \times 100$$

The results of three successive typical experiments are summarized in the following table.

TABLE II

| | BSP Retention (Minutes) | | |
|---|---|---|---|
| Experiment No. | Control | CCl$_4$ | CCl$_4$ & Mucoprotide |
| I | 15 ± 4 | 35 ± 4 | 18 ± 4 |
| II | 18 ± 4 | 28 ± 5 | 19 ± 2 |
| III | 17 ± 3 | 28 ± 6 | 17 ± 4 |
| | | 100% increase in BSP retention | no increase in BSP retention |

The data in this table indicates that, within experimental error, the mucoprotide-treated animals experienced a return to normal liver function as evidenced by the normal BSP clearance values. Further examination of the rat livers after chronic intoxication with carbon tetrachloride showed a significant diminution of the central lobular necrosis of hepatocytes in those animals treated with mucoprotide as compared with the untreated controls. The microscopic evidence is consistent with the return to normal of the BSP values for overall liver function.

It is to be noted that the first method involves the production and prevention of perilobular liver necrosis whereas the second method involves the production and prevention of central lobular liver necrosis. Since liver biopsy has shown that both types of liver damage may be experienced in clinical and veterinary mammalian practice, both methods of assay are employed in the standardization of any specific production batch of mucoprotide.

Biological activity of the mucoprotide preparations is determined by the minimum amount required to prevent or correct liver damage by both of the tests described above. Although both the BSP retention test (carbon tetrachloride damage) and the acute alcohol intoxication test are used in the final biological evaluation (bioassay) of a particular production batch of mucoprotide, the BSP retention test is used as the critical test since it is a quantitative and objective test, and is directly related to the corresponding routine clinical laboratory test for evaluating liver function. Despite the semi-quantitative nature of the alcohol intoxication test, there seems to be a good correlation between the two tests.

The standardization of the cruder buccal form is effected by taking out a small aliquot of this semi-purified mucoprotide batch and carrying this aliquot through the entire production procedure on a laboratory scale and finally assaying the isolated mucoprotides by the two bioassay methods described above. The final dosage of the buccal form is determined by using an aliquot containing ten times the corresponding parenteral dosage of mucoprotides. The factor of ten times the parenteral dose was selected by clinical trial and is a reasonable factor in view of the crudeness of the product and the uncertainties of absorption by the buccal route of administration as compared to that of the parenteral route.

We claim:

1. In the method of producing a biologically active mucoprotide product from mammalian liver, such product having anti-allergenic and detoxicant properties, said method comprising the following steps:
   (a) providing a dilute aqueous solution of the mucoprotide components of the source material, such solution being the supernate resulting from treatment of the autolysate of the source material to separate proteins which are precipitable by dilute lead acetate and dilute ammonium sulfate and
   (b) treating the said aqueous solution with acetone to cause the formation of three layers,
   the improvement to obtain a mixture of mucoprotidic proteinaceous materials comprising the further steps of;
   (c) separating the top and middle layers from the bottom layer,
   (d) subjecting the combined top and middle layers of step (c) to heat sufficient to precipitate unstable and antigenic material and
   (e) separating and discarding the precipitate resulting from step (d).

2. The method of claim 1 wherein step (b) is carried out at approximately room temperature.

3. The method of claim 1 followed by holding the supernate from step (e) at about room temperature for a sufficient time for precipitate to form and for precipitation to proceed to completion, separating the precipitate and then packaging the supernate as a final product after further concentration and sterile filtering if needed.

4. In the method of producing a biologically active mucoprotide product from mammalian liver, such product having anti-allergenic and detoxicant properties, said method comprising the following steps:
   (a) providing a dilute aqueous solution of the mucoprotide components of the source material, such solution being the supernate resulting from treatment of the autolysate of the source material to separate proteins which are precipitable by dilute lead acetate and dilute ammonium sulfate and
   (b) treating the said aqueous solution with acetone to cause the formation of three layers, the improvement to obtain a mixture of mucoprotidic materials comprising the further steps of;
   (c) separating the top and middle layers from the bottom layer,
   (d) lyophilizing the separated layers and
   (e) mixing the lyophilized product with a suitable buccal excipient.

5. The product of claim 3 in parenteral form.

6. The product of claim 4.